(12) United States Patent
Racz

(10) Patent No.: US 8,287,496 B2
(45) Date of Patent: Oct. 16, 2012

(54) FLOW ELEMENTS FOR USE WITH FLEXIBLE SPINAL NEEDLES, NEEDLE ASSEMBLIES AND METHODS THEREFOR

(75) Inventor: N. Sandor Racz, Coppell, TX (US)

(73) Assignee: Custom Medical Applications, Inc., Johnstown, NY (US)

( * ) Notice: Subject to any disclaimer, the term of this patent is extended or adjusted under 35 U.S.C. 154(b) by 0 days.

(21) Appl. No.: 12/009,349

(22) Filed: Jan. 17, 2008

(65) Prior Publication Data

US 2009/0187140 A1 Jul. 23, 2009

(51) Int. Cl.
*A61M 5/178* (2006.01)
(52) U.S. Cl. ......... 604/164.09; 604/164.01; 604/168.01; 604/170.01; 604/170.02; 604/528
(58) Field of Classification Search .................. 604/158, 604/164.01–164.13, 165.01, 165.02, 166.01, 604/167.01, 168.01, 170.01–170.03, 264, 604/272, 506, 508, 510, 528, 900; 600/585
See application file for complete search history.

(56) References Cited

U.S. PATENT DOCUMENTS

| | | | |
|---|---|---|---|
| 1,867,624 A | 7/1932 | Hoffman | |
| D138,589 S | 8/1944 | Brandenburg | |
| 3,175,554 A | 3/1965 | Stewart | |
| 3,722,505 A | 3/1973 | Kolin | |
| 3,943,225 A | 3/1976 | Koehn | |
| 4,106,506 A | 8/1978 | Koehn et al. | |
| D269,549 S | 6/1983 | Gross | |
| 4,504,268 A * | 3/1985 | Herlitze | 604/170.01 |
| 4,553,960 A * | 11/1985 | Lazarus et al. | 604/158 |
| 4,808,157 A | 2/1989 | Coombs | |
| D302,589 S | 8/1989 | McMenamy et al. | |
| 4,973,312 A | 11/1990 | Andrew | |
| 4,994,036 A | 2/1991 | Biscoping et al. | |
| 5,085,631 A | 2/1992 | Leighton | |
| 5,092,847 A * | 3/1992 | Pozzo | 604/170.02 |

(Continued)

FOREIGN PATENT DOCUMENTS

WO WO 91/08785 6/1991

(Continued)

OTHER PUBLICATIONS

PCT International Search Report and Written Opinion, PCT/US2009/000250 dated Sep. 7, 2009.

(Continued)

*Primary Examiner* — Kevin C Sirmons
*Assistant Examiner* — Kami A Bosworth
(74) *Attorney, Agent, or Firm* — TraskBritt

(57) ABSTRACT

A flow element for use with flexible needles and flexible needle assemblies to minimize flow occlusion within a flexible needle is provided. The flow element is particularly suited for uses with a flexible needle for minimizing incidence of post-dural puncture headache. The flow element includes a body having an internal flow path for conducting a fluid through a flexible needle, and an anti-restriction member. The anti-restriction member includes an elongated body, a proximal end coupled to the body within the internal flow path, and a distal end for disposing at least a portion of the elongated body within a flexible needle. A flexible spinal needle assembly for minimizing flow occlusion through an internal flow path of a flexible needle by unintended kinking that is potentially caused by ligament or muscle layer movements is also provided.

22 Claims, 7 Drawing Sheets

U.S. PATENT DOCUMENTS

| | | | |
|---|---|---|---|
| 5,100,390 A | 3/1992 | Lubeck et al. | |
| 5,116,323 A | 5/1992 | Kreuzer et al. | |
| 5,135,525 A | 8/1992 | Biscoping et al. | |
| 5,160,323 A | 11/1992 | Andrew | |
| 5,209,734 A * | 5/1993 | Hurley et al. | 604/158 |
| 5,232,442 A | 8/1993 | Johnson et al. | |
| 5,250,035 A | 10/1993 | Smith et al. | |
| 5,304,141 A | 4/1994 | Johnson et al. | |
| D353,454 S | 12/1994 | Coombs | |
| D353,668 S | 12/1994 | Banks et al. | |
| 5,382,238 A * | 1/1995 | Abrahamson et al. | 604/170.01 |
| 5,490,521 A | 2/1996 | Davis et al. | |
| 5,490,845 A | 2/1996 | Racz | |
| 5,496,281 A | 3/1996 | Krebs | |
| 5,571,091 A | 11/1996 | Davis et al. | |
| 5,573,519 A | 11/1996 | Zohmann | |
| D378,405 S | 3/1997 | Musgrave et al. | |
| 5,628,734 A | 5/1997 | Hatfalvi | |
| 5,669,882 A | 9/1997 | Pyles | |
| 5,810,788 A | 9/1998 | Racz | |
| 5,830,188 A | 11/1998 | Abouleish | |
| 5,846,226 A | 12/1998 | Urmey | |
| 5,871,470 A | 2/1999 | McWha | |
| 5,899,891 A | 5/1999 | Racz | |
| 5,976,110 A | 11/1999 | Greengrass et al. | |
| 5,993,436 A | 11/1999 | Kitou et al. | |
| 6,131,433 A | 10/2000 | Nakada et al. | |
| 6,190,372 B1 | 2/2001 | Racz | |
| 6,245,029 B1 | 6/2001 | Fujita et al. | |
| 6,245,044 B1 * | 6/2001 | Daw et al. | 604/158 |
| D471,980 S | 3/2003 | Caizza | |
| 6,558,353 B2 | 5/2003 | Zohmann | |
| 6,730,059 B2 | 5/2004 | Caizza | |
| RE39,499 E | 2/2007 | Racz | |
| D547,446 S | 7/2007 | Racz et al. | |
| 7,241,283 B2 | 7/2007 | Putz | |
| 7,255,686 B2 | 8/2007 | Putz | |
| D550,355 S | 9/2007 | Racz et al. | |
| 7,322,954 B2 | 1/2008 | Putz | |
| 7,413,562 B2 | 8/2008 | Ferguson et al. | |
| 7,465,292 B2 | 12/2008 | Putz | |
| 7,608,064 B2 | 10/2009 | Putz | |
| 2002/0099335 A1 | 7/2002 | Zhomann | |
| 2003/0094731 A1 | 5/2003 | Simpson | |
| 2003/0125675 A1 | 7/2003 | Caizza et al. | |
| 2005/0004563 A1 | 1/2005 | Racz et al. | |
| 2005/0033393 A1 | 2/2005 | Daglow | |
| 2005/0090801 A1 | 4/2005 | Racz et al. | |
| 2005/0137569 A1 * | 6/2005 | Jones et al. | 604/500 |
| 2006/0058743 A1 | 3/2006 | Putz | |
| 2006/0116608 A1 | 6/2006 | Poutiatine et al. | |
| 2006/0129102 A1 | 6/2006 | Putz | |
| 2007/0179440 A1 | 8/2007 | Putz | |
| 2007/0191791 A1 | 8/2007 | Putz | |
| 2008/0065017 A1 | 3/2008 | Racz et al. | |
| 2008/0221516 A1 | 9/2008 | Partika et al. | |
| 2009/0187140 A1 | 7/2009 | Racz | |
| 2010/0298785 A1 | 11/2010 | Racz | |

FOREIGN PATENT DOCUMENTS

| | | |
|---|---|---|
| WO | WO 2004/050141 A2 | 6/2004 |
| WO | WO 2004/096314 A2 | 11/2004 |
| WO | WO 2004/096314 A3 | 6/2007 |
| WO | WO 2009/091567 A2 | 7/2009 |
| WO | WO 2009/091567 A3 | 7/2009 |

OTHER PUBLICATIONS

Vlessides, Rapid Reversal of Spinal Anesthesia Follows Cerebrospinal Lavage, Clinical Anesthesiology. Oct. 2009. AnesthesiologyNews.com, pp. 92-93.

Office Action for U.S. Appl. No. 12/735,451 dated Dec. 21, 2011.

Office Action for U.S. Appl. No. 12/804,751 dated Nov. 14, 2011.

Response to Office Action for U.S. Appl. No. 12/804,751 dated Jan. 30, 2012.

Office Action for U.S. Appl. No. 12/804,751 dated Apr. 13, 2012.

* cited by examiner

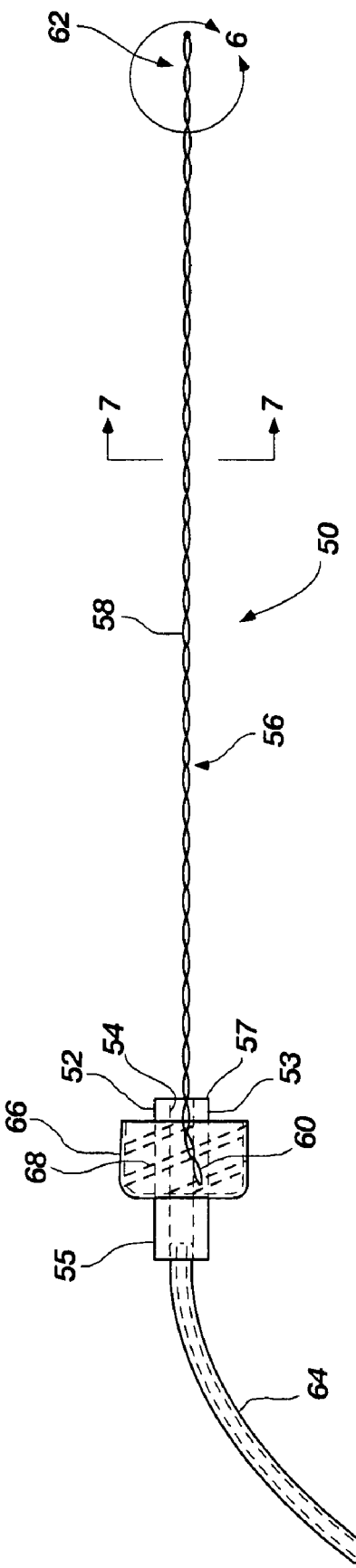
FIG. 5
FIG. 6
FIG. 7

FLOW ELEMENTS FOR USE WITH FLEXIBLE SPINAL NEEDLES, NEEDLE ASSEMBLIES AND METHODS THEREFOR

FIELD OF THE INVENTION

This invention relates generally to medical devices, and particularly to structures for fluid occlusion prevention in medical needles. It is particularly directed to a flow element for use with flexible needles and flexible spinal needle assemblies, including methods therefor.

BACKGROUND

The advantages of continuous spinal anesthesia have long been appreciated by anesthesiologists. Unlike conventional single-shot techniques, continuous spinal anesthesia ("CSA") with an indwelling catheter allows anesthesia of unlimited duration and the ability to carefully control the level of the block by administering repeated small, incremental doses of anesthetic. As compared to continuous epidural anesthesia, which has become widely used as a substitute for spinal, CSA generally requires far less drug to achieve the desired effect, has a definite endpoint of correct catheter placement, requires no "test dose," and produces a much more reliable, less spotty block.

Unfortunately, technical problems have severely limited the usefulness of continuous spinal techniques. Until recently, the standard technique of inserting the spinal catheter through the spinal needle, coupled with the difficulty of manufacturing truly small needles and catheters, has meant large needles and catheters were required, resulting in an unacceptably high incidence of post-dural puncture headaches ("PDPH").

In the mid 1980's, various advances fueled renewed interest in spinal anesthesia in general and in CSA in particular. Improvements in manufacturing ever-smaller conventional (QUINCKE.™) spinal needles of 25 gauge, 26 gauge, and even 30 gauge significantly reduced PDPH incidence. These results allowed for the use of spinal anesthesia in age groups and procedures not previously considered suitable.

At the same time, advances in catheter manufacture made possible spinal catheters of 28 gauge and 322 gauge which would fit through relatively small spinal needles. Unfortunately, these catheters proved difficult to handle, difficult to make, expensive, and, more ominously, associated with several reports of neurologic damage (i.e., cauda equina syndrome). Many clinicians therefore tried and abandoned them, and they were ultimately removed from the market by the Food and Drug Administration ("FDA").

The FDA's decision to recall and ban the marketing of microspinal catheters for CSA in the U.S., and its requirement that any new device for CSA be subjected to an extremely stringent pre-market approval process, has resulted in a freeze on the development of these products, at least in the United States. Nevertheless, the injection of local anesthetics for the establishment of surgical anesthesia is not the only use to which such devices might beneficially be put. In fact, the injection of narcotics, such as FENTANYL.™, for analgesia of labor would be a very desirable use of such catheters.

Installing a conventional catheter generally requires various cumbersome steps involving threading long, very thin catheters through a spinal needle. Simply threading a catheter into the end of a spinal needle can be so difficult that some manufacturers include a "threading aid" as part of their kit. Once threaded, a degree of uncertainty exists for the clinician about how far to insert the catheter. Also, a risk exists that a piece of the catheter might be sheared off by the needle if the catheter were to be pulled back during the threading operation. In such case, bits of catheter could potentially be left behind in the intrathecal space. Furthermore, removing the spinal needle while holding the catheter in position can be a challenge. Additionally, attaching a hub/injection adapter to the naked end of the 28 g or 32 g catheter can be even more of a challenge. Finally, once the adapter is successfully attached, the small lumen of the catheter permits only a slow flow of either CSF or anesthetic. In short, the conventional spinal catheter threading operation requires considerable time and effort on the part of a clinician.

A parallel technical development has been the introduction of non-cutting spinal needles, such as the "Pencil Point" type needles, which have been shown to drastically reduce PDPH incidence. Examples of Pencil Point type needles include the Sprotte and Whitacre non-cutting spinal needles. In terms of PDPH incidence, a 22 gauge Sprotte seems to be roughly equivalent to a 25 gauge or 26 gauge Quincke, while a 24 gauge Sprotte or 25 gauge Whitacre essentially eliminates the risk of PDPH.

One problem of Sprotte and Whitacre non-cutting spinal needles is that the injection orifice is on the side of the needle. Failures of spinal anesthesia have been described as when the needle was "half-in, half-out" of the intrathecal space. Another problem with Sprotte and Whitacre spinal needles is that the smooth curved tip profile provides no definitive feedback signal or "click" when the dura is punctured. Such lack of feedback contributes to uncertainty of catheter tip placement.

One solution overcoming the limitations of the conventional catheters mentioned above and approved by the FDA is a flexible spinal needle described in U.S. patent application Ser. No. 10/694,235, filed Oct. 27, 2003, (U.S. 2005-0090801 A1, published Apr. 28, 2005) the disclosure of which is incorporated by this reference in its entirety herein. Specifically, the flexible spinal needle may be used for CSA while essentially eliminating the risk of PDPH.

BRIEF SUMMARY OF THE INVENTION

In order to improve the performance of a flexible needle, a flow element is provided for use therewith. A flow element may be used with flexible needles, including flexible spinal needles, and flexible needle assemblies to prevent or at least minimize the extent to which flow occlusion may occur within a flexible needle, particularly when used with a flexible needle for minimizing incidence of post-dural puncture headache. The flow element includes a body having an internal flow path for conducting a fluid through a flexible needle, and an anti-restriction member. The anti-restriction member includes an elongated body, a proximal end coupled to the body within the internal flow path, and a distal end for disposing at least a portion of the elongated body within a flexible needle.

In certain embodiments, a parallel flexible spinal needle assembly for minimizing flow occlusion through an internal flow path of a flexible needle by unintended kinking potentially caused by ligament or muscle layer movements is also provided.

In certain embodiments, a flexible spinal needle assembly, a flexible spinal needle assembly kit, a method for installing a flexible spinal needle assembly, and a process for producing a flow element are provided.

Other advantages of the flexible needle and flexible needle assembly are now described, in which a flow element may be used to advantage. In contrast to a conventional spinal catheter, the instant flexible needle flow element is advantageously used with a flexible needle that provides for simple and straightforward needle insertion without either threading a catheter through a needle or installing an adapter. The installation procedure is similar to intravenous catheter or "single-shot" spinal procedures already familiar to clinicians. Placement of the flexible needle over the inserting needle allows a larger diameter flexible needle to be inserted. The resulting improved diameter flexible needle allows easier and faster flow of either cerebrospinal fluid ("CSF") or medicating agents.

Insertion of the flexible needle tip in the intrathecal space with the instant device is more secure. The Pencil Point style non-cutting tip of the support needle promotes a low incidence of PDPH. However, the assembly tip may be shaped to provide a feedback signal when the dura is punctured. Observation of CSF with the instant design further assures a clinician that the entire orifice at the flexible needle tip is in the intrathecal space.

The chance of neurologic damage is lessened with the shorter flexible needle. The shorter length is less likely to be wedged against a nerve root. More importantly, the larger bore of the improved flexible needle promotes turbulent flow and improved mixing of any injected fluid will occur with CSF. The improved short flexible needle, which is inserted to the hub, removes ambiguity about how far to insert it. The flexible needle hub greatly aids fixation to the skin. Contamination during insertion is less likely. Also, kinking at the skin is essentially impossible when a flexible kink sleeve is included.

The relative ease, simplicity, and safety of the improved device may expand the use of continuous spinal anesthesia/analgesia. Lumbar epidurals could be replaced with this apparatus. Similarly, most single-shot spinals may be replaced with this apparatus "just-in-case" the procedure goes longer than expected, or the level of the block needs adjustment. A number of situations outside the operating environment could benefit from this device, non-exclusively including: acute and chronic pain control with spinal narcotics, labor analgesia, diagnostic taps, and indwelling catheters for continuous peripheral nerve blocks as well as research purposes. In effect, this apparatus may be used in medical procedures involving needle insertion at the lumbar level of the spine. Versions of the instant device are contemplated to offer improved techniques for the insertion of a wide variety of medical catheters, including arterial lines, major nerve blocks, intraperitoneal catheters, intraventricular (brain) catheters, and intravenous catheters.

The instant device provides an apparatus and method for inserting a flexible spinal needle in a quick, easy, and straightforward manner. Such a flexible spinal needle assembly has an outside diameter sized so that withdrawal of the assembly from the subarachnoid space, subsequent to insertion of the assembly thereby, permits the dura mater substantially to reseal a space formerly occupied by the assembly. An assembly typically includes a support needle, a flexible needle slidably mounted on the support needle, and a central stylet slidably inserted within the support needle. The inserted tip end of a flexible needle assembly is advantageously configured to produce a feedback signal to indicate dural puncture.

A support needle may have a piercing point on a first end and a central hub at a second end. The piercing point protrudes from a front, distal, inserted, or tip, end of a flexible spinal needle assembly. A piercing point penetrates substantially without cutting, and helps to form a puncture hole through dura mater which automatically may substantially reseal subsequent to retraction of a flexible needle. A second end of the central stylet generally may have a locking hub. The locking hub may carry a first attach structure to connect with corresponding structure of a central stylet.

The front end of the support needle may be configured cooperatively to form a structural interference with a distal end of a flexible needle. Such structural interference resists relative motion between the piercing point and the distal end of the flexible needle during insertion of the flexible needle into a patient. A rear end of the support needle may carry a support hub having second attach structure to removably connect to the central hub of the central stylet. The first and second attach structures may be structured to form a removable connection, such as a LUER-LOCK.™ type connection. The support hub may be advantageously made from a transparent material to permit observation of fluid flow therethrough.

A flexible needle may be characterized as a flexible conduit having distal and proximal ends. Preferred flexible needles have sufficient transverse flexibility to accommodate patient torso bending movement, thus operating to reduce a patient's awareness of the presence of the device. Flexible needles typically are made from medical grade plastic materials. For example, polyester shrink tube or similar materials may be used. The distal end of a flexible needle may be reinforced, in some instances, to resist peel-back from the front end of a support needle.

The transition from the proximal flexible needle hub to the flexible needle body may be reinforced by a kink sleeve segment. The kink sleeve segment may be constructed of a firm yet flexible material, such as nylon or other polymers. The kink sleeve is intended to cushion the transition from the hub to the flexible needle body during bending that will occur after the flexible needle is inserted and the support needle removed. For example, once the flexible needle is inserted, the hub may be bent over and taped to the skin, often at an angle of around 90 degrees.

Needle hubs are typically configured for fluid flow attachment to medical fluid transfer equipment. For example, needle hubs may be configured to form LUER-LOCK.™ type connections with such equipment. It may be further preferred to form the needle hub for substantially unobtrusive attachment to a patient's skin by way of an intermediary adhesive element or by designing the hub to lay flush against the patient's skin with a connection parallel thereto without a need for bending the flexible needle.

A flexible needle assembly may be installed using a method similar to the following: providing a flexible needle assembly as disclosed herein; using conventional spinal needle technique to prepare the skin of a patient at an injection site, apply local anesthetic, pierce skin and subcutaneous fascia, and insert a piercing point tip of the flexible spinal needle assembly; removing the central stylet subsequent to receiving a feedback signal that puncture of the dura mater has occurred; checking for CSF at the support hub; if no CSF is observed, further inserting the assembly until the tip is within the intrathecal space; or if CSF is observed, unlocking the support hub and the flexible needle hub, and while holding the support needle stationary, advancing the flexible needle until the flexible needle hub contacts the skin; removing the support needle and checking for the presence of CSF at the flexible needle hub; disposing and connecting a flow element into an internal flow path of the flexible needle to substantially reduce flow occlusion through the internal flow path caused by kinking; connecting medical fluid transfer appara-

BRIEF DESCRIPTION OF THE DRAWINGS

FIG. 5 is a plan view of a flow element of the flexible needle assembly shown in FIG. 2.

FIG. 6 shows an exploded view the flow element as indicated by reference in FIG. 5.

FIG. 7 shows a cross-sectional view taken along section line 7-7 in FIG. 5.

DETAILED DESCRIPTION OF THE INVENTION

The illustrations presented herein are, in some instances, not actual views of any particular flow element, flexible needle assembly or other feature of a flexible spinal needle assembly, but are merely idealized representation that are employed to describe the invention. Additionally, elements common between figures may retain the same numerical designation.

Figure 1:
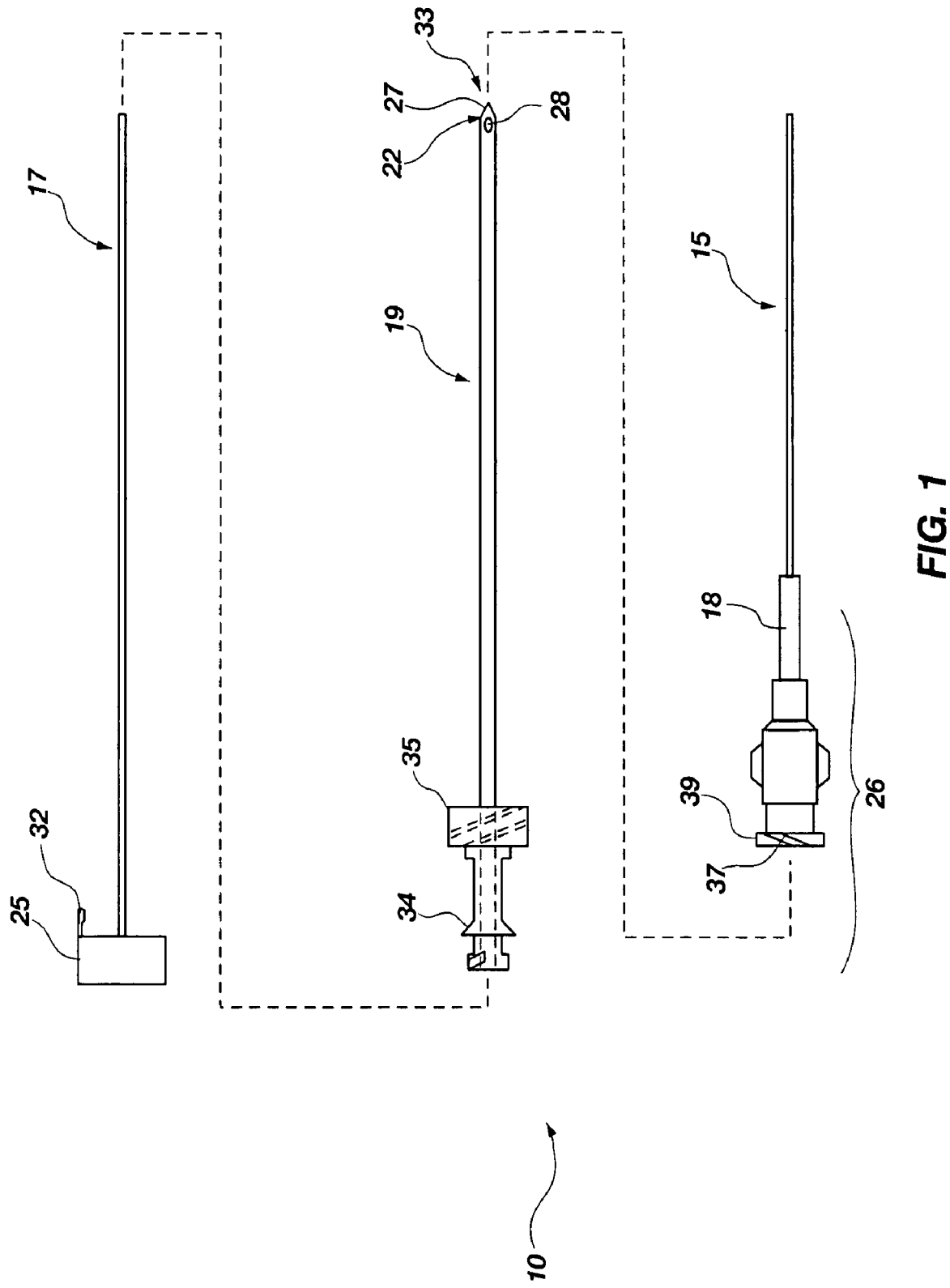
FIG. 1 is an exploded plan assembly view of a flexible needle assembly.
Figure 2:
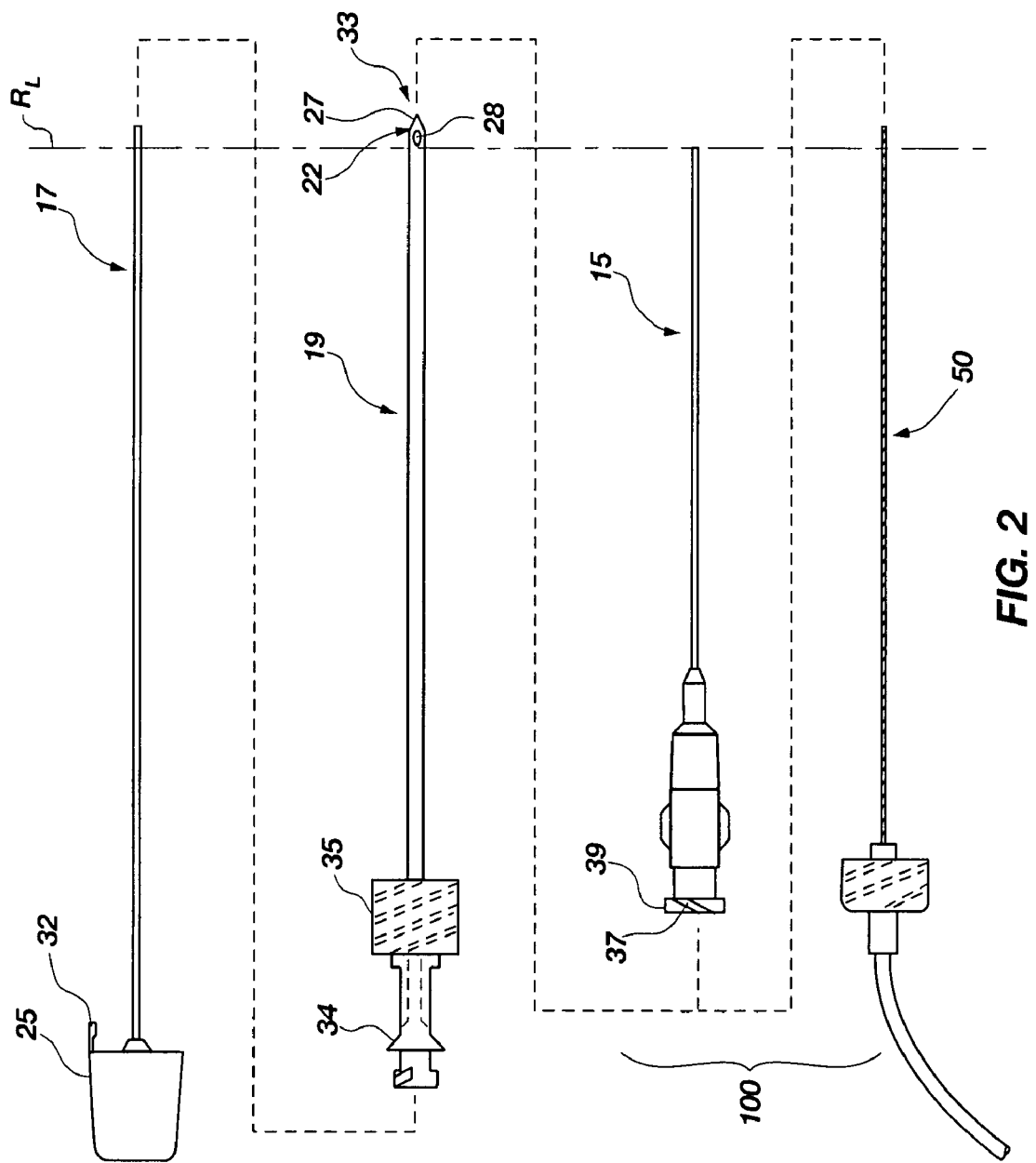
FIG. 2 is an exploded plan assembly view of a flexible needle assembly.

Generally, the flow element may be advantageously used with an integrated spinal needle or flexible needle assembly 10 (much like an intravenous needle and catheter mounted therein) as shown in FIG. 1, however, in which the flexible needle 15 is releasably mounted on the outside of a support needle 19. The flexible needle 15 is configured for uses with embodiments of the invention as will be further described below, and is also configured for placement on the outside of the support needle 19 that provides a number of advantages which are first described before turning to the embodiments of the invention. First, this design makes insertion significantly easier by eliminating the separate steps of catheter threading, insertion and hub/adapter attachment. A single "stick" is all that is required; once the needle is in, so is the flexible conduit for infusion of fluid therein. Since the flexible needle 15 is larger for a given needle size, its flow and handling characteristics will be much improved, and it is easier and cheaper to manufacture. Advantageously, embodiments of the invention provide for a flow element 50 that may be introduced into the flexible needle 15 to minimize the effects of kinking by substantially preventing total flow occlusion of fluid therethrough and ensuring a minimal amount of fluid flow therein as shown in FIG. 2.

Shown in FIG. 1 is an exploded plan assembly view of a flexible needle assembly 10 usable in accordance with an embodiment of the invention. The flexible needle assembly 10 which is configured for use with embodiments of the invention consists of three components: a central stylet 17, a hollow support needle 19, and a flexible needle 15. The overall dimensions of the flexible needle 15 and representatively the flexible needle assembly are generally represented in length, and may be similar to a conventional spinal needle in gauge size ranging from about 22 gauge to about 25 gauge in size, but as illustrated the flexible needle 15 is shown as being about 23 gauge cannula in size.

The innermost component of the assembly is configured as a solid central stylet 17. When inserted in the support needle 19 (discussed in detail further herein), the central stylet 17 prevents the entry of extraneous tissue or other material into the support needle opening 28 during insertion. The central stylet may also serve as a "stiffening" portion of the assembly providing extra support and stiffness to the entire assembly. The hub 25 of the central stylet 17 is outermost, or located at an extreme proximal end 26 of assembly 10, because the central stylet 17 is the first to be removed. An attachment structure, such as tab 32, may be located on the hub 25 for retaining the central stylet 17 in the support needle 19. The tab 32 may interact with a corresponding attachment structure on the hub 35 of the support needle 19.

The next layer of the assembly is a removable hollow support needle 19 to support and allow insertion of the flexible needle 15 into a subject. This support needle 19 closely resembles a conventional spinal needle. The tip 27 of support needle 19 may have a pencil-point formation to allow penetration of tissue substantially without cutting. As discussed previously herein, this aids in forming a puncture hole through the dura mater which automatically may substantially reseal subsequent to retraction. An opening 28 is located near the tip 27 to allow cerebral spinal fluid "CSF" or other fluids to flow through the support needle 19 from the opening 28 to the hub 35. It will be appreciated that where desired, suitable treatment solutions may be injected through the support needle 19, to enter a patient's tissue through the opening 28.

The hub 35 of the support needle 19 may beneficially be made of clear plastic to allow visualization of CSF return when the central stylet 17 has been removed. Of course, any CSF present will visibly flow from the distal end 33 of support needle 19 subsequent to removal of the central stylet 17. Optional use of clear plastic or a transparent fluid observation window in the support hub 35 can provide an additional convenience, and minimize loss of CSF.

The central stylet 17 may be attachable to the support needle 19, as illustrated in FIG. 1. The central hub 25 typically carries an attach structure, such as tab 32, to interface in a structural interference with an attach structure 34 carried by support hub 35. As illustrated, tab 32 and attach structure 34 cooperatively form a slidably engageable joint. Alternative releasable retaining joint configurations, including rotatable attachments such as LUER-LOCK.™ type joints, may also be used.

The outermost layer of the assembly 10 is the flexible needle 15 itself. As previously described is approximately 23 gauge in size and about the length of a conventional spinal needle, although different diameters and lengths for use with different procedures is within the scope of the invention. Conventional plastic catheter material may be used in its construction. The flexible needle material may be reinforced with a flat ribbon internal spring 45 (shown in FIG. 4), an internal or external wire wrap, or other reinforcing structure. Alternative materials, and various materials in combination, also may be used to construct a flexible needle 15. Suitable flexible needle material produces a flexible needle 15 which is fairly stiff and has a sufficiently high tensile strength to maintain structural integrity during insertion, while in the body, and during retraction from a patient. A flexible needle 15 desirably possesses sufficient transverse flexibility to deform and accommodate patient motion to reduce irritation from the presence of a foreign body.

A slippery nonstick surface is generally provided to ease insertion and removal of the flexible needle 15. The tip 29 of flexible needle 15 may be tapered into a curve to blend smoothly into the edge of support needle 19 (see, FIGS. 4 & 19). The degree of this curved taper may be governed by a tradeoff between the decreased resistance to insertion of an extreme taper versus the fragility and tendency to peelback of a very thin leading edge. A preferred taper provides ease of insertion, a feedback signal to indicate entry of flexible needle 15 through the dura, and sufficient tensile strength to prevent peelback. The feedback signal may be described as a distinct "click" or a change in required insertion force. The "click" may be a sonic event, or may be perceptible only through the clinician's fingers in contact with the assembly.

Figure 4:
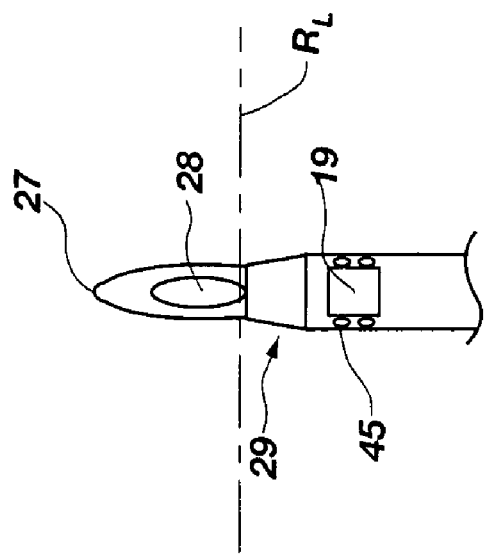
FIG. 4 shows a detail view of a distal end portion of the flexible needle assembly tip shown in FIG. 1 when assembled.

Flexible needle tips 29 having shapes in addition to those illustrated in FIGS. 1 and 4 are within contemplation. For example, manufacturing or material requirements may influence the shape of a tip 29. An alternative flexible needle may include a reinforcing wire of fine gauge. Such a wire may be embedded into the material forming the sealing wall of flexible needle 15 to reinforce against peelback. The wire may also be spiraled along the length of the flexible needle to provide additional strength to resist collapse, kinking, or breakage of a flexible needle 15. Alternatively, a flat spring ribbon 45 may be used to provide reinforcement.

The flexible needle hub 39 typically includes a LUER-LOCK.™ type connector, or other attachment structure, for easy and secure connection with common infusion tubing, injection ports, or syringes, and other medical fluid transfer apparatus. Since the flexible needle 15 may be inserted all the way to the hub 39, a flat, circular flange, or other ergonomically shaped structure, may be provided on the surface of the hub which rests against the patient's skin to facilitate easy tape fixation. Fixation to the patient's skin may be accomplished with a slotted circular foam tape. Of course, other tapes or adhesive systems may also be used. A quantity of suitable adhesive or tape could be included in a prepackaged flexible spinal needle assembly kit.

It is desirable to prevent inadvertent premature removal of the support needle 19 from the flexible needle 15. In the embodiment depicted in FIG. 1, support hub 35 receives thread structure 37 located on the flexible needle hub 39 and locks with rotation. Such a positive connection may be desirable and may form a LUER-LOCK.™ or other rotatable-type joint. Other such interlocking or even alternative retaining structure may also be used. For example, a secure friction fit attachment between support needle 19 and flexible needle 15 is within contemplation in the practice of this invention, as is a structural interference fit of attachment structures similar to shown in connection with tab 32 on the central stylet 17.

Figure 3:
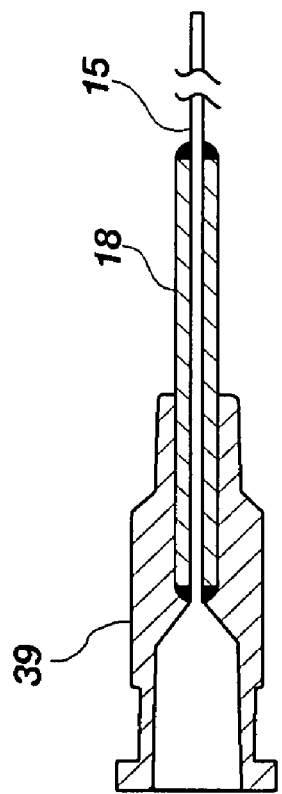
FIG. 3 shows a partial cross-sectional view of a flexible needle shown in FIG. 1.

As best shown in FIG. 3 showing a partial cross-sectional view of a flexible needle shown in FIG. 1, the flexible needle 15 may include a flexible kink sleeve 18. Kink sleeve 18 covers a portion of the proximal surface of the flexible needle 15 to protect the area covered against kinking and damage during bending. Desirably, the kink sleeve 18 will begin at the base of the flexible needle 15 inside the hub 39 (as depicted in FIG. 3) to provide maximum protection, although alternate embodiments where kink sleeve begins distal to the base of the flexible needle inside the hub 39, or at the base of the hub 39 are within the scope of the invention. Kink sleeve 18 may extend distally along the length of the flexible needle 15 to a length appropriate for the planned use of the flexible needle. Typically, kink sleeve 18 will extend to a length sufficient to prevent kinking of the flexible needle at the skin of the patient or within the skin and fascia of the patient. Kink sleeve 18 may be constructed of any suitable flexible material that is medically acceptable, including polymers such as nylon.

When flexible needle 15 is fully inserted, a portion of the kink sleeve 18 may reside within the skin and fascia of the patient. The hub 39 may then be bent over and taped to the skin, if desired. The kink sleeve 18 acts to protect the flexible needle 15 during this bending process, which may bend the flexible needle 15 at an angle of about 90 degrees or more. The kink sleeve 18 absorbs the force of the bend and maintains the flexible needle 15 in a position allowing flow therethrough. Kinking of the flexible needle 15 is thus minimized, and may be prevented. The kink sleeve 18 may be impregnated, coated, or otherwise treated with a biocompatible infection resistant substance to prevent adverse tissue reaction or infection at the flexible spinal needle entry site.

Flexible needles 15 may be made from suitable medical grade plastic type materials. For example, polyester shrink tubing may be employed with one embodiment of the device, although it will be appreciated that any suitable material, including other polymers, may be used. Flexible needles 15 may be composed of a single material, or may be a composite of two or more materials to provide the desired flexible needle handling characteristics. Fine gauge wire, such as stainless steel wire, or a flat internal ribbon spring 45 (shown in FIG. 4), may be incorporated into a flexible needle sealable wall to improve resistance to peelback and to further support the structural integrity of the flexible needle. The distal ends may alternatively be reinforced with metal bands. Hubs 25, 35 and 39 are typically also made from medical grade plastic type materials. The central stylet 17 and support needle 19 are typically made from a medically acceptable metal, such as stainless steel or titanium.

The design of this device makes the placement of a spinal flexible needle 15 quick, easy, and straightforward. It should be so easy, in fact, that most clinicians may choose to use this device for every spinal procedure they perform. The initial steps of skin preparation, local anesthetic infiltration, and needle insertion are identical to those now used with conventional spinal needles. As the flexible needle assembly 10 is being inserted and the clinician feels the slight "click" upon dural puncture, he or she removes the central stylet 17. If the insertion has been successful, CSF will promptly appear at the hub 35 of the support needle 19. If the dura has not been penetrated, the entire assembly 10 may continue to be advanced until dural puncture is achieved. If desired, the central stylet 17 may be reinserted prior to continued advancement in order to prevent tissue from entering the opening 28.

Once CSF is observed at the hub 35 of the support needle 19, the clinician can be certain that the tip 29 of the flexible needle 15 is within the intrathecal space. If desirable for the procedure, the clinician may continue to advance the hollow support needle/flexible needle 19/15 of the assembly 10 another centimeter or so. At this point, the hub 35 of the hollow needle 19 is typically twisted to unlock it from the flexible needle hub 39, and while holding the hollow needle 19 stationary, the flexible needle 15 is advanced all the way until the hub 39 contacts the patient's skin. For embodiments including a kink sleeve 18, this advancement may insert, or further insert, the kink sleeve 18 within the patient's skin.

At this point, the hollow support needle 19 may be removed, and the appearance of CSF at the flexible needle hub 39 will confirm the correct placement of the flexible needle 15. The desired injection port, tubing, or other medical fluid transfer apparatus, may then be attached to the flexible needle hub 39 such as by way of attach structure 37. Where necessary, the flexible needle 15 may be bent and taped to the patient's skin before or after the attachment of the corresponding apparatus, if required. Where included, kink sleeve 18 protects the flexible needle 15 from kinking and damage at the bend. A piece of slotted, circular foam tape (which might also be treated with an antimicrobial) may also be applied to fix the hub 39 to the skin, prevent dislodging of the flexible needle 15, and cushion the patient to reduce potential irritation from the hub 39.

The flexible needle 15 may then be left in place for as long as clinically necessary and, assuming adequate tensile strength, be easily and safely removed when appropriate. At the time of removal, since the non-cutting point 22 of the support needle 19 substantially eliminated laceration of any fibers in the dural membrane, the mesh-like fibers may relax to their original position, thus automatically closing the dural puncture. Therefore the PDPH incidence is expected to be in agreement with Sprotte and Whitacre needles, despite the luxury of a reasonably large flexible needle 15 in a device usable to advantage with the instant invention.

Figure 8:
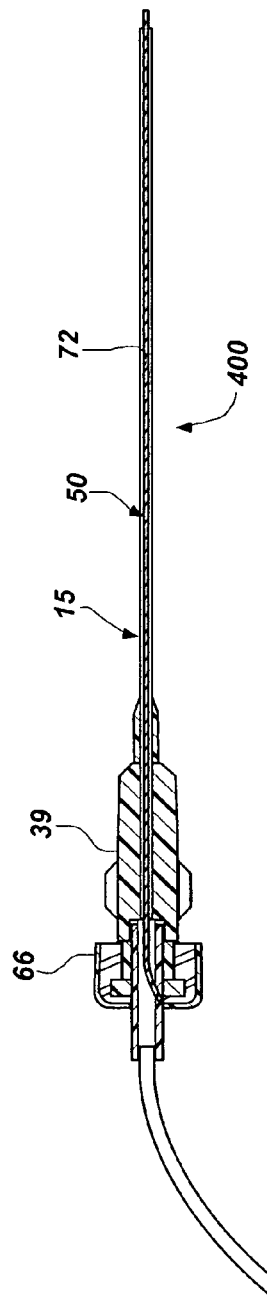
FIG. 8 is a side assembled view of the flexible needle assembly shown in FIG. 2.

FIG. 2 is an exploded plan assembly view of a flexible needle assembly 100 in accordance with a first embodiment of the invention. The flexible needle assembly 100 comprises a flexible needle 15 as previously described and a flow element 50, and may further comprise a central stylet 17, and a hollow support needle 19. FIG. 8 shows a side assembled view of the flexible needle assembly 100 shown in FIG. 2. The overall dimensions of the flexible needle 15 and the flow element 50 are generally represented in length as indicated by reference line $R_L$, and may be similar to a conventional spinal needle in gauge size ranging from about 22 gauge to about 25 gauge in size, but as illustrated the flexible needle 15 is shown as being about 23 gauge cannula in size and the flow element 50 being sufficiently small as to be disposed within an inner flow path 72 (shown in FIG. 8) of the flexible needle 15.

Figure 9:
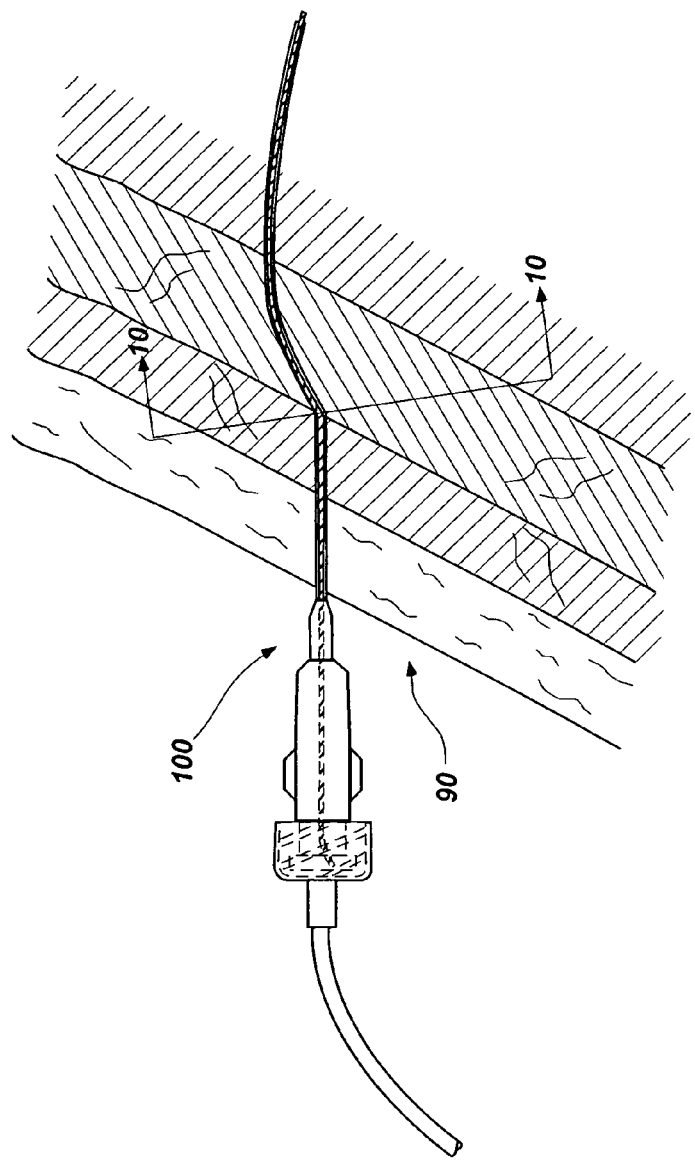
FIG. 9 representatively shows a portion of the flexible needle assembly show in FIG. 8 being kinked in ligament layers.
Figure 10:
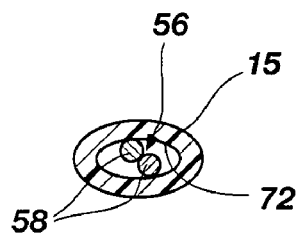
FIG. 10 shows a cross-sectional view of the flexible needle assembly taken along section line 10-10 in FIG. 9.

FIG. 5 is a plan view of the flow element 50 of the flexible needle assembly 100 shown in FIG. 2. The flow element 50 is advantageously used with the flexible needle 15 to further prevent kinking of the flexible needle 15 or from substantially occluding fluid flow therethrough when inserted through muscle or ligament layers 90 of a subject as illustrated in FIG. 9. Illustratively, FIG. 10 shows a cross-sectional view of the flexible needle assembly taken along section line 10-10 as shown in FIG. 9 where the flexible needle 15 is kinked and an anti-restriction member 56 of the flow element 50 prevents fluid occlusion within the inner flow path 72 thereof.

Figure 11:
FIG. 11 illustrates a cross-sectional view of a conventional flexible needle being partially occluded when bent in ligament layers.
Figure 12:
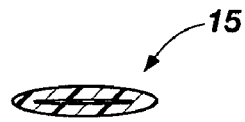
FIG. 12 illustrates a cross-sectional view of a conventional flexible needle being fully occluded when kinked in ligament layers.

FIG. 11 illustrates a cross-sectional view of a conventional flexible needle 15 being partially occluded when bent in ligament layers and FIG. 12 illustrates a cross-sectional view of a conventional flexible needle 15 being fully occluded when kinked in ligament layers.

Returning to FIG. 5, The flow element 50 includes a body 52 having an internal flow path 54 for conducting a fluid through the flexible needle 15 and an anti-restriction member 56. The anti-restriction member 56 includes an elongated bodies 58, a proximal end 60 coupled to the body 52 within the internal flow path 54, and a distal end 62 for disposing at least a portion of the elongated body 58 within the flexible needle 15. Advantageously, the elongated body 58 will help to maintain a minimal amount of fluid flow through the flexible needle 15 should kinking thereof occur. FIG. 9 representatively shows a portion of the flexible needle assembly 100 show in FIG. 8 being kinked in ligament layer 90 as mentioned above.

Returning to FIG. 5, the flow element 50 includes a body 52 having an internal flow path 54 for conducting a fluid through the flexible needle 15 and an anti-restriction member 56. The anti-restriction member 56 includes an elongated body 58 (e.g., one or more freely extending wires), a proximal end 60 coupled to the body 52 within the internal flow path 54, and a distal end 62 for disposing at least a portion of the elongated body 58 within the flexible needle 15. Advantageously, the elongated body 58 will help to maintain a minimal amount of fluid flow through the flexible needle 15 should kinking thereof occur. FIG. 9 representatively shows a portion of the flexible needle assembly 100 shown in FIG. 8 being kinked in muscle or ligament layers 90, as mentioned above.

The body 52 may includes a cylindrical outer surface 53 extending substantially between a first end 55 and a second end 57, wherein a portion of the cylindrical outer surface 53 is configured for sealing attachment to the attach structure 39 of the flexible needle 15. A flexible conduit 64 may be coupled to the first end 55 of the body 52 to supply fluid thereto or for connection to a machine configured for delivering fluids thereto. A support hub 66 may be coupled to the body 52, the support hub 66 having a first attach structure 68 configured to removably attach to the attach structure 37 of the flexible needle to allow at least a portion of the elongated body 58 to be disposed therein. Optionally, the first attach structure 68 may comprise a LUER-LOCK.™ type of connector or any other suitable connector type for attaching to the flexible needle 15.

Figure 13:
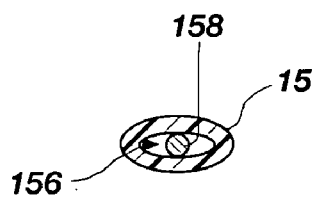
FIG. 13 shows a cross-sectional view of another flexible needle assembly.
Figure 14:
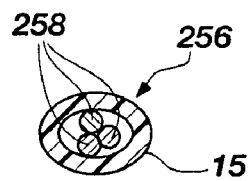
FIG. 14 shows a cross-sectional view of a further flexible needle assembly.
Figure 15:
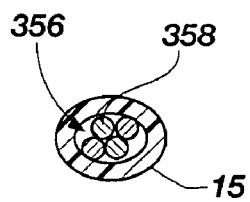
FIG. 15 shows a cross-sectional view of yet another flexible needle assembly.

FIG. 7 shows a cross-sectional view of the anti-restriction member 56 taken along section line 7-7 in FIG. 5. As shown, the anti-restriction member 56 may includes two elongated bodies 58 in this embodiment. Also shown in FIG. 6, the two elongated bodies 58 comprise a twisted wire pair. Optionally, the twisted wire pair may be secured distally with a weld bead 70. Manufacturing the anti-restriction member 56 may include receiving two wires and disposing them one on the other relative to their axial lengths, optionally twisting them and further securing them with a weld bead, such as to leave one end prepped for securing to, or forming with, the body 52 and the other end for disposing in a flexible needle as herein described. It is to be recognized that the anti-restriction member 56 may comprise one or three or more elongated bodies other than the two elongated bodies 58 as illustrated by the twisted wire pair. For example: FIG. 13 shows a flexible needle 15 having a single elongated body 158 of an anti-restriction member 156 disposed therein; FIG. 14 shows a flexible needle 15 having three elongated bodies 258 of an anti-restriction member 256 disposed therein; and FIG. 15 shows a flexible needle 15 having four elongated bodies 358 of an anti-restriction member 356 disposed therein, where each embodiment provides a different amount of minimal fluid occlusion should the flexible needle 15 be kinked when used.

It is to be recognized that each elongated body 58 of the anti-restriction member 56 while shown as a single uniform structure, may comprises two or more wires or elements banded, twisted or coupled together to form the unitary elongated body 58. However, in this embodiment the anti-restriction member 56 comprises six wires (not shown) for each of the two elongated bodies 58 shown in FIG. 10.

Figure 16:
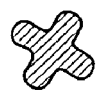
FIG. 16 shows a cross-sectional view of a flow element.
Figure 17:
FIG. 17 shows a cross-sectional view of a flow element.
Figure 18:
FIG. 18 shows a cross-sectional view of a flow element.

Optionally, each elongated body 58 of the anti-restriction member 56 may be configured with a cross-sectional shape of a circle as shown in FIG. 10, an ellipse (not shown), diamond as shown in FIG. 17, a jack as shown in FIG. 16, a square (not shown), a triangle (not shown), a sigmoid as shown in FIG. 18 or any other suitable cross-sectional shape for advantageously preventing and minimizing flow occlusion through a flexible spinal needle assembly 100.

Advantageously, the anti-restriction member 56 effectively maintains an open channel within the inner flow path 72 of the flexible needle 15 upon bending or kinking.

The flow element 50 may be designed where the distal end 62 of the elongated body 58 protrudes partially from a flexible distal end of the flexible needle 15 to allow the fluid to be dispersed more effectively from the cannula of the flexible needle 15, or may be designed in length to a greater or lesser extent than illustrated.

Figure 19:
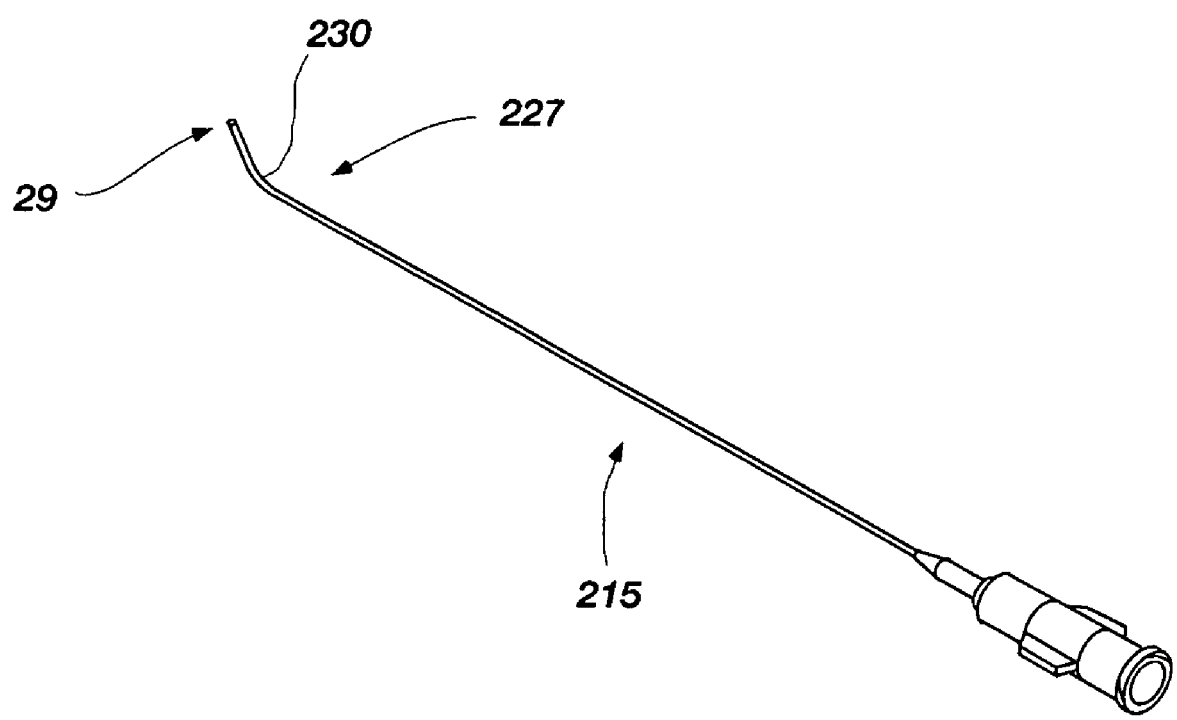
FIG. 19 is a side view of a flexible spinal needle assembly.

FIG. 19 is a perspective view of a flexible spinal needle 215. The flexible spinal needle 215 may be used with a flow element 50 for minimizing flow occlusion through an internal flow path thereof by unintended kinking that is potentially caused by ligament or muscle layer movements when inserted into dura mater and into the intrathecal space of a subject. The flexible spinal needle 215 includes an internal flow path (not shown) advantageously for receiving a flow element 50 for coupling with the flexible needle 215 and disposed through a substantial portion of the internal flow path. The flexible needle includes an exterior diameter such that withdrawal of the flexible needle from the dura mater, subsequent to insertion of the flexible needle assembly therethrough, permits the dura mater to substantially reseal a space formerly occupied by the flexible needle, and a tip and a flexible needle body of the flexible needle are of substantial elongated extent to be further extendable into the dura mater upon extraction of a support needle coupled therewithin before exposing the flow element 50 therewithin. Optionally, the distal end or tip 227 of the flexible spinal needle 215 may include a curved portion 230 to facilitate further insertion into an intrathecal space a subject upon removal of a support needle 19 that naturally strengthens while supporting the flexible material characteristics of the flexible spinal needle 215. The curved portion 230 may be manufactured by forming the material in the desired shape or otherwise providing material strain or strain relief strategically located in a portion of the material forming the cannula of the flexible spinal needle 215 the curved portion 230 may be formed using manufacturing methods understood by a person of skill in the art.

In still other embodiments of the invention, a flexible spinal needle assembly kit is provided. The flexible spinal needle assembly kit includes a flow element configured for minimizing flow occlusion through a flow path upon insertion into a flexible needle and a flexible needle having a flow path and configured for receiving a flow element or a support needle within the flow path. The flexible spinal needle assembly kit may further include a support needle configured for insertion into the flexible needle and to minimize the transverse flexibility of the flexible needle to enable insertion of the support needle and coaxially supported flexible needle through dura mater and into a spine of a subject. The flexible spinal needle assembly kit may also comprise a central stylet configured for removable insertion into the support needle to prevent entry of matter through an opening proximate a distal end of the support needle when inserted into a subject.

Optionally, the flexible spinal needle assembly kit may include the support needle and the flexible needle pre-assembled allowing insertion of the pre-assembly into a patient facilitating removal of the support needle and subsequent insertion of the flow element into the flexible needle. Likewise, the central stylet, the support needle and the flexible needle may be pre-assembled for allowing insertion of the pre-assembly into a patient to facilitate removal of the support needle and central stylet and subsequent insertion of the flow element into the flexible needle.

A method for installing a flexible spinal needle assembly in accordance with embodiments of the invention may include: inserting a distal end of a flexible spinal needle assembly provided through dura mater and into an intrathecal space of a subject, the spinal needle assembly comprising: a support needle with a non-cutting piercing point at the distal end and a hollow bore; a flexible needle with a tip at the distal end and slidably mounted on and supported by the support needle to expose the piercing point slightly extending beyond the tip in the distal end thereof, the flexible needle having an outside diameter sufficiently small so that upon insertion of the flexible spinal needle assembly and withdrawal of the support needle from the flexible needle permits the dura mater substantially to seal against the outside diameter of the flexible needle; removing the support needle from within the flexible needle while maintaining the tip of the flexible needle within the intrathecal space to expose an inner flow path; and thereafter, connecting a flow element to the flexible needle disposing an anti-restriction member of the flow element into the inner flow path of the flexible needle to substantially prevent fluid occlusion caused by bending or kinking of the flexible needle.

The method for installing a flexible spinal needle assembly may further include, prior to removing the support needle from within the flexible needle, verifying presence of cerebrospinal fluid in a proximal end of the flexible spinal needle assembly; if no cerebrospinal fluid is observed, further inserting the distal end of the flexible spinal needle assembly through dura mater until the tip is at least in the intrathecal space; and thereafter removing the support needle from within the flexible needle upon observing cerebrospinal fluid presence within the flexible spinal needle assembly.

Optionally, inserting the distal end of the flexible spinal needle assembly through dura mater and into the intrathecal space of the subject comprises the outside diameter of the flexible needle being sufficiently small so that upon withdrawal of the flexible needle from dura mater, subsequent to insertion of the flexible spinal needle assembly therethrough, permits the dura mater substantially to reseal a space formerly occupied by the flexible needle.

The method for installing a flexible spinal needle assembly may comprise a central stylet slidably mounted in the support needle to prevent the entry of matter through an opening in the distal end of the support needle during inserting, and further comprising prior to removing the support needle from within the flexible needle checking for cerebrospinal fluid at a proximate end of the spinal needle assembly; if no cerebrospinal fluid is observed, replacing the central stylet and further inserting the spinal needle assembly until the tip is in the intrathecal space; and once cerebrospinal fluid is observed, then removing.

The method for installing a flexible spinal needle assembly may also comprise a central stylet slidably mounted in the support needle to prevent the entry of matter through an opening in the distal end of the support needle during inserting, and further comprising prior to removing the support needle from within the flexible needle checking for cerebrospinal fluid at a proximate end of the spinal needle assembly; if no cerebrospinal fluid is observed, replacing the central stylet and further inserting the spinal needle assembly until the tip is in the intrathecal space; and once cerebrospinal fluid is observed, then removing the support needle and the central stylet.

Optionally, removing the support needle from within the flexible needle comprises advancing the flexible needle into the intrathecal space until a proximate end hub of the flexible needle contacts the subject.

The method for installing a flexible spinal needle assembly may further comprise subsequent to removing the support needle from within the flexible needle checking for the presence of cerebrospinal fluid at a flexible needle hub on a proximate end of the flexible needle prior to disposing the anti-restriction member of the flow element into the inner flow path of the flexible needle.

The method for installing a flexible spinal needle assembly may optionally comprise subsequent to removing the support needle from within the flexible needle and after disposing the anti-restriction member of the flow element into the inner flow path of the flexible needle and connecting the flow element to the flexible needle connecting medical fluid transfer apparatus to the flow element for supply fluid into the inner flow path; and securing the flexible needle hub to the subject.

The method for installing a flexible spinal needle assembly may still further comprise prior to inserting the distal end of the flexible spinal needle assembly through dura mater and into the intrathecal space of the subject, preparing the skin of a patient at an injection site; applying local anesthetic at the injection site; and inserting the distal end of the flexible spinal needle assembly through the prepared injection site.

The method for installing a flexible spinal needle assembly may comprises checking for cerebrospinal fluid comprises removing the central stylet subsequent to receiving a feedback signal that puncture of the dura mater has occurred.

Lastly, the method for installing a flexible spinal needle assembly may comprises a flow element comprising: a body having an internal flow path for conducting a fluid through the flexible needle; and the anti-restriction member having an elongated body, a proximal end coupled to the body within the internal flow path, and a distal end to facilitate disposing at least a portion of the elongated body within the inner flow path of the flexible needle.

After having been apprised of the disclosure hereof, one of ordinary skill in the art would be able to make and use the invention.

What is claimed is:

1. A flexible spinal needle assembly adapted for minimizing flow occlusion through a lumen of a flexible needle when inserted into a subject, the flexible spinal needle assembly comprising:
   a flexible needle comprising:
      a lumen;
      a distal end comprising a tip and an opening located proximate to the tip; and
      at least one radially reinforcing element to maintain structural integrity of the flexible needle during insertion into the subject; and
   a flow element adapted for use with the flexible needle previously inserted within the subject, the flow element comprising:
      a flow element body having an internal flow path adapted for conducting a fluid into the lumen of the flexible needle, the flow element body having structure adapted for coupling the flow element body to the flexible needle to position the internal flow path in fluid communication with the lumen;
   a conduit, secured to the flow element body and couplable to a supply of fluid, the conduit being in fluid communication with the internal flow path adapted for supplying a quantity of fluid to the internal flow path; and
   an anti-restriction member having an elongated body comprising at least one freely extending wire, a proximal end coupled to the flow element body within the internal flow path, and a distal end formed by a terminal end of the at least one wire adapted for inserting at least a portion of the elongated body within the flexible needle after the flexible needle has been inserted within the subject, the terminal end of the at least one wire being sized and adapted to extend freely to a location proximate to the distal end of the flexible needle when the anti-restriction member is disposed in the flexible needle, the anti-restriction member being adapted for placement within the lumen of the flexible needle to permit fluid flow through the lumen while the anti-restriction member is resident within the lumen, the anti-restriction member functioning to resist occlusion of the fluid flow through the lumen resulting from a kinkage of the flexible needle.

2. The flexible spinal needle assembly of claim 1, wherein the flow element body is made from a medical grade plastic, the anti-restriction member is made from a medical grade stainless steel and the flow element body includes a cylindrical outer surface extending substantially between a first end and a second end, wherein a portion of the cylindrical outer surface is configured for sealing attachment to an attachment structure of the flexible needle.

3. The flexible spinal needle assembly of claim 2, wherein the conduit is coupled to the first end of the flow element body and a support hub coupled to the flow element body, the support hub having a first attachment structure configured to removably attach to the flexible needle while positioning at least a portion of the elongated body therein, the first attachment structure comprises a luer lock type connector.

4. The flexible spinal needle assembly of claim 1, wherein the elongated body of the anti-restriction member comprises at least two wires forming a freely extending set of wires.

5. The flexible spinal needle assembly of claim 4, wherein the elongated body of the anti-restriction member comprises six wires.

6. The flexible spinal needle assembly of claim 1, wherein the anti-restriction member comprises a plurality of elongated bodies.

7. The flexible spinal needle assembly of claim 1, wherein the elongated body of the anti-restriction member comprises at least two wires forming a freely extending set of twisted wires.

8. The flexible spinal needle assembly of claim 1, wherein the elongated body of the anti-restriction member comprises at least two wires forming a freely extending set of wires that are secured distally with a weld bead.

9. The flexible spinal needle assembly of claim 1, wherein the distal end of the elongated body protrudes from a flexible distal end of the flexible needle, the flexible needle is configured having an outside diameter sized so that withdrawal of the flexible needle from dura mater of a spine, subsequent to insertion of the flexible needle assembly through the dura mater, permits the dura mater substantially to reseal a space formerly occupied by the flexible needle, the elongated body of the anti-restriction member is configured for substantially preventing partial occlusion of the lumen, and the flexible needle is configured for being slidably mounted on a portion of a support needle such that a first end of the support needle protrudes from the flexible needle exposing a non-cutting piercing point for allowing the flexible needle and the support needle to be inserted through the dura mater and into the intrathecal space of a subject and, upon removal of the support needle, is configured for disposing a portion of the anti-restriction member within the flexible needle.

10. The flexible spinal needle assembly of claim 9, wherein a flexible needle body of the flexible needle is of such substantial axial extent to be further extendable into the dura mater upon extraction of the support needle, and the flow element body comprises a support hub having a first attach structure, and a proximal end of the flexible needle carries a flexible needle hub having a second attach structure configured to removably attach to the first attach structure carried by the support hub.

11. The flexible spinal needle assembly of claim 10, wherein the flexible needle body comprises a cannula formed from a first material and radially reinforced over an extent toward a distal portion of the lumen by a second material comprising a stainless steel ribbon spring and further comprises a kink sleeve disposed on a portion of the flexible needle hub and over a portion of the cannula of the flexible needle.

12. The flexible spinal needle assembly of claim 1 wherein the flexible needle has an exterior diameter such that withdrawal of the flexible needle from dura mater, subsequent to insertion of the flexible spinal needle assembly therethrough, permits the dura mater substantially to reseal a space formerly occupied by the flexible needle, and the tip and a flexible needle body of the flexible needle are of substantial elongated extent to be further extendable into the dura mater upon extraction of a support needle coupled therewithin before exposing the flow element therewithin, and wherein the flow element is configured for attachment to medical fluid transfer equipment having structure to form a luer lock type connection.

13. The flexible spinal needle assembly of claim 1 wherein:
the flexible needle has a flexible needle body comprising an elongated hollow tube having the lumen formed therein; and
wherein the terminal end of the at least one wire is in direct contact with an inner portion of the flexible needle in the lumen.

14. The flexible spinal needle assembly of claim 13, comprising a flexible spinal needle assembly kit comprising a prepackaged and sterilized assembly comprising the flow element and the flexible needle.

15. The flexible spinal needle assembly kit of claim 14, further comprising a support needle configured for insertion into the flexible needle and to minimize the transverse flexibility of the flexible needle to enable insertion of the support needle and coaxially supported flexible needle through dura mater and into a spine of a subject, and a central stylet configured for removable insertion into the support needle to prevent entry of matter through an opening proximate a distal end of the support needle when inserted into the subject, wherein the support needle and the flexible needle are preassembled allowing insertion of the pre-assembly into the subject facilitating removal of the support needle and subsequent insertion of the flow element into the flexible needle.

16. The flexible spinal needle assembly of claim 1, wherein the at least one radially reinforcing element comprises a structure formed within the flexible needle.

17. The flexible spinal needle assembly of claim 16, wherein the at least one radially reinforcing element comprises at least one of an internal wire wrap and an internal spring.

18. The flexible spinal needle assembly of claim 1, wherein the at least one radially reinforcing element comprises an external wire wrap.

19. A process for producing the flow element of the flexible spinal needle assembly of claim 1, the process comprising:
forming the anti-restriction member having the elongated body, the proximal end and the distal end, the elongated body configured for disposing at least a portion thereof by way of the distal end within the flexible needle; and
securing the proximal end of the anti-restriction member to the flow element body having the internal flow path for conducting a fluid through the flexible needle.

20. The process for producing a flow element of claim 19, wherein securing the proximal end of the anti-restriction member to the flow element body comprises injection molding the flow element body about the proximal end of the anti-restriction member, and forming the anti-restriction member having the elongated body comprises forming the anti-restriction member with a plurality of elongated bodies, at least one elongated body comprising a plurality of wires.

21. A flow element for use with a flexible needle previously inserted and remaining within a patient, the flow element comprising:
a flow element body having an internal flow path for conducting a fluid into a lumen of the flexible needle, the flow element body having structure for coupling the flow element body to the flexible needle to position the internal flow path in fluid communication with the lumen;
a conduit, secured to the flow element body and couplable to a supply of fluid, the conduit being in fluid communication with the internal flow path for supplying a quantity of fluid to the internal flow path; and
an anti-restriction member having an elongated body comprising a freely extending twisted set of wires formed by at least two wires, a proximal end coupled to the flow element body within the internal flow path, and a distal end formed by terminal ends of the at least two wires, the terminal ends of the at least two wires being sized and adapted to extend freely to a location proximate to a distal end of the flexible needle, the anti-restriction member being configured for insertion within the lumen of the flexible needle after the flexible needle has been inserted in the patient to permit fluid flow through the lumen while the anti-restriction member is resident within the lumen, the anti-restriction member functioning to resist occlusion of the fluid flow through the lumen resulting from a kinkage of the flexible needle.

22. A flexible spinal needle assembly for minimizing flow occlusion through a lumen of a flexible needle when inserted into a subject, the flexible spinal needle assembly comprising:
a flexible needle including a lumen; and
a flow element for use with the flexible needle previously inserted within a patient, the flow element comprising:
a flow element body having an internal flow path for conducting a fluid into the lumen of the flexible needle, the flow element body having structure for coupling the flow element body to the flexible needle to position the internal flow path in fluid communication with the lumen;

a conduit, secured to the flow element body and couplable to a supply of fluid, the conduit being in fluid communication with the internal flow path for supplying a quantity of fluid to the internal flow path; and an anti-restriction member having an elongated body comprising a freely extending set of wires formed by at least two wires, each of the at least two wires having a terminal end being sized and adapted to extend freely to a location proximate to a distal end of the flexible needle, a proximal end of the anti-restriction member coupled to the flow element body within the internal flow path, and a distal end of the anti-restriction member formed by the terminal end of each of the at least two wires and configured for inserting at least a portion of the elongated body within the flexible needle after the flexible needle has been inserted within the patient, the anti-restriction member being configured for placement within the lumen of the flexible needle to permit fluid flow through the lumen while the anti-restriction member is resident within the lumen, the anti-restriction member functioning to resist occlusion of the fluid flow through the lumen resulting from a kinkage of the flexible needle.

* * * * *